United States Patent [19]

Nambu et al.

[11] 4,283,567

[45] Aug. 11, 1981

[54] METHOD FOR RECOVERING RESORCINOL

[75] Inventors: Hirohiko Nambu; Hiroaki Nakagawa, both of Iwakuni; Masayasu Isibasi, Yamaguchi, all of Japan

[73] Assignee: Mitsui Petrochemical Industries Ltd., Tokyo, Japan

[21] Appl. No.: 105,246

[22] Filed: Dec. 19, 1979

[30] Foreign Application Priority Data

Dec. 20, 1978 [JP] Japan ................................. 53-156247

[51] Int. Cl.$^3$ .............................................. C07C 37/68
[52] U.S. Cl. ..................................... 568/754; 568/768; 568/806
[58] Field of Search ....................... 568/754, 768, 806

[56] References Cited

FOREIGN PATENT DOCUMENTS

| | | | |
|---|---|---|---|
| 36-16722 | 1/1961 | Japan ........................................ | 568/754 |
| 739907 | 2/1953 | United Kingdom ..................... | 568/754 |
| 759010 | 10/1956 | United Kingdom ..................... | 568/754 |
| 775813 | 5/1957 | United Kingdom ..................... | 568/754 |
| 873676 | 7/1961 | United Kingdom ..................... | 568/768 |
| 982514 | 2/1965 | United Kingdom ..................... | 568/754 |

*Primary Examiner*—Werren B. Lone
*Attorney, Agent, or Firm*—Sherman & Shalloway

[57] ABSTRACT

In a method for recovering resorcinol by thermally cracking high-boiling by-products formed by the acid-cleavage of m-diisopropylbenzene dihydroperoxide in the presence of at least one ammonium compound selected from the group consisting of ammonium sulfate and ammonium bisulfate at a temperature of about 170° C. to about 350° C. under reduced pressure, the improvement wherein said thermal cracking is carried out at a pressure of less than 50 mmHg gauge in the absence of any inert gas supplied.

9 Claims, No Drawings

METHOD FOR RECOVERING RESORCINOL

This invention relates to an improved method for recovering additional amounts of resorcinol by thermally cracking high-boiling by-products contained in the acid-cleavage product of m-diisopropylbenzene dihydroperoxide. According to this improved method, additional amounts of resorcinol can be commercially advantageously recovered in high yields by an easy operation.

More specifically, this invention provides in a method for recovering additional amounts of resorcinol by thermally cracking high-boiling by-products contained in the acid-cleavage product of m-diisopropylbenzene dihydroperoxide in the presence of at least one ammonium compound selected from the group consisting of ammonium sulfate and ammonium bisulfate at a temperature of about 170° C. to about 350° C. under reduced pressure, the improvement wherein said thermal cracking is carried out at a pressure of less than 50 mmHg gauge in the absence of any inert gas supplied, i.e. in a substantially anhydrous condition.

Methods are known to produce resorcinol by acid cleavage of m-diisopropylbenzene dihydroperoxide (to be sometimes referred to as m-DHP) obtained by the oxidation of m-diisopropylbenzene (to be sometimes referred to as m-DIPB). The acid cleavage product is known to contain high-boiling by-products (by-products having a higher boiling point than resorcinol) in addition to resorcinol and acetone. It is assumed that these high-boiling by-products consist predominantly of a condensation product between resorcinol and acetone, and condensates between resorcinol and olefins such as m-isopropenyl phenol.

It is commercially advantageous therefore to recover additional amounts of resorcinol by thermally cracking these high-boiling by-products, and methods of recovery have been suggested.

For example, British Pat. No. 739,907 discloses the recovery of additional amounts of resorcinol and m-isopropenylphenol from acid-cleavage by-products having a lower volatility than resorcinol (i.e., high-boiling by-products) by thermal cracking. British Pat. No. 775,813 discloses that the thermal cracking in the process disclosed in British Pat. No. 739,907 is carried out while passing an inert gas such as steam, nitrogen or carbon dioxide. These British Patents do not at all disclose the performance of the aforesaid thermal cracking in the presence of an ammonium compound.

British Pat. No. 982,514 discloses a process for the recovery of resorcinol from the product of the acid cleavage of m-diisopropylbenzene dihydroperoxide, which comprises distilling the cleavage product to remove low-boiling materials, heating the cleavage product substantially free from low-boiling materials but containing the resorcinol to vaporize substantially all of the products other than the high-boiling condensation products, cracking the residue under reduced pressure and with the aid of steam stripping to vaporize further quantities of resorcinol, condensing the combined products of the vaporizer, and recovering resorcinol therefrom. This British Pat. No. 982,514 teaches the use of a reduced pressure of less than 500 mmHg, preferably 50 to 250 mmHg, and the use of ammonia or an ammonia-generating compound for maintaining the pH of the feed material to the cracker suitably between 3 and 4. In the British Patent, however, it is essential to perform thermal cracking in the presence of steam which comes within the definition of the inert gas in the above-cited British Pat. No. 739,907.

Japanese Patent Publication No. 16722/61 (corresponding to British Pat. Nos. 873,676 and 857,113) discloses a similar suggestion to that made in the aforesaid British Pat. No. 982,514. As regards the pressure conditions, this Japanese Patent Publication states that atmospheric pressure or pressures slightly lower than atmospheric pressure are preferred, and moreover, it is essential in the Japanese Publication to perform the thermal cracking in the presence of steam as in the above-cited British Patent.

In the British Pat. No. 982,514 and Japanese Patent Publication No. 16722/61 which teach the thermal cracking of high-boiling by-products formed by the acid-cleavage of m-diisopropylbenzene dihydroperoxide in the presence of ammonia or an ammonia-generating compound, cracking in the co-presence of steam as an inert gas, i.e. in a hydrous condition, is essential. In these patents, resorcinol formed by thermal cracking is obtained as an aqueous solution, and the resorcinol must be separated from the aqueous solution. The operation of separating resorcinol is complicated, and losses of resorcinol during the operation, for example owing to condensation, cannot be avoided. Thus, resorcinol is difficult to recover in a high yield. Ammonia generated by the decomposition of ammonium sulfate during the thermal cracking is absorbed by the aqueous solution to increase its pH. The ammonia, too, adversely affects the recovery of resorcinol in that it undesirably tends to convert the resorcinol into a high-boiling product.

The present inventors made investigations in order to remove the technical troubles in the thermal cracking of high-boiling by-products in the presence of ammonia or an ammonia-generating compound. These investigations have led to the discovery that the cracking of high-boiling by-products should be performed under lower pressures than those recommended by the prior suggestions while avoiding a hydrous condition, i.e. the presence of steam, which is essential in the prior suggestions, and that by using a set of these new parameters, means for supplying steam can be completely omitted, and the aforesaid technical troubles can be removed advantageously, thus making it possible to recover resorcinol at a markedly improved yield.

It is an object of this invention therefore to provide an improved method for recovering resorcinol by thermally cracking high-boiling by-products contained in the acid-cleavage product of m-diisopropylbenzene dihydroperoxide.

The above and other objects and advantages of the invention will become more apparent from the following description.

It is known to produce m-DHP by air oxidizing m-DIPB and/or m-diisopropylbenzene monohydroperoxide in the liquid phase, and the reaction conditions used in this process are also well known. It is of course known that the resulting oxidation product containing m-DHP, either as such or after separating m-DHP from it, is subjected to acid cleavage to form resorcinol and acetone as main products, and high-boiling by-products are formed during the acid-cleavage.

For example, m-DHP, or the product of oxidation of m-DIPB containing m-DHP is sent to an acid-cleavage reactor together with a suitable acid-cleavage solvent, for example a ketone such as acetone, methyl ethyl ketone or methyl isobutyl ketone, or a hydrocarbon such as benzene, toluene, xylene or ethylbenzene. When the oxidation reaction product is directly used, an oxidizing agent such as hydrogen peroxide, tert-butyl hydroperoxide or peracetic acid may, if desired, be caused to act on it prior to, or during, the acid-cleavage reaction to convert 2-hydroxy-2-propyl-α,α-dimethylbenzyl hydroperoxide in the oxidaton reaction product to m-DHP so that the yield of resorcinol will be increased.

As is well known, acid cleavage can be performed at a temperature of about 20° to about 120° C. in the presence of an acid catalyst such as sulfuric acid, perchloric acid, phosphoric acid, ion exchange resins, clays or synthetic silica alumina.

In a method for recovering resorcinol by thermally cracking high-boiling by-products contained in the acid-cleavage product of m-DHP which is formed by known means, in the presence of at least one ammonium compound selected from the group consisting of ammonium sulfate and ammonium bisulfate at a temperature of about 170° to about 350° C., the present invention provides the improvement wherein said thermal cracking is carried out at a reduced pressure of less than 50 mmHg gauge, preferably about 5 to about 40 mmHg, more preferably about 5 to about 30 mmHg, in the absence of an inert gas such as steam, nitrogen, or carbon dioxide supplied, i.e. in an anhydrous condition.

These high-boiling by-products may be those containing resorcinol and low-boiling by-products (by-products having lower boiling points than resorcinol) which remain after removal of toluene and acetone from the acid-cleavage product of m-DHP, those containing resorcinol remaining after removal of a greater portion of the low-boiling by-products, or those substantially free from toluene, acetone, the low-boiling by-products and resorcinol. The removal can be performed by known methods such as distillation or extraction. When the removal is performed by distillation, high-boiling by-products will form. According to this invention, such additional high-boiling by-products formed in the distillation step can also be advantageously cracked.

Preferred high-boiling by-products to be cracked by the method of this invention are those containing up to about 60% by weight, based on the starting material to be cracked, of resorcinol and low-boiling by-products which remain after the removal of the acid catalyst from the acid-cleavage product by neutralization or filtration, and preferably after further removal of acetone and low-boiling substances such as the solvent used in the acid-cleavage reaction; or those containing more than 60% by weight, especially more than 70%, based on the material to be cracked, of high-boiling by-products and not more than 40% by weight, especially not more than 30% by weight, of low-boiling by-products and resorcinol which remain after further removal of a greater portion of the low-boiling by-products and resorcinol.

In performing the method of this invention, it is preferred not only to carry out the thermal cracking in the absence of any inert gas supplied, but also to use those high-boiling by-products (or products containing them) which are deprived of as much water as possible so as to minimize the inclusion of water in the resorcinol recovered.

The thermal cracking is carried out in the presence of an ammonium salt of sulfuric acid such as ammonium sulfate, ammonium bisulfate or a mixture of these. Ammonium bisulfate is preferred.

The amount of the ammonium compound is about 0.01 to about 5% by weight, preferably about 0.05 to about 0.25% by weight, based on the weight of the raw materials to be thermally cracked.

The thermal cracking temperature is, for example, about 170° to about 350° C., preferably about 200° to about 300° C. When the temperature of thermal cracking is lower than the above-specified limit, the rate of thermal cracking is too slow, and the efficiency is poor. Use of too high temperatures tends to cause coking, and may cause blockage of the apparatus and accesory devices.

The thermal cracking in accordance with this invention is carried out in the absence of any inert gas, especially steam, supplied, i.e. in a substantially anyhdrous condition. Resorcinol or ispropenyl phenol formed by thermal cracking is distilled off from the thermal cracking zone. By adjusting the distillation pressure at this time to less than 50 mmHg, preferably to about 5 to about 40 mmHg, more preferably about 5 to about 30 mmHg, the distillation can be performed rapidly, and ammonia generated by the decomposition of the ammonium sulfate can be sucked by the pressure-reduced zone so that ammonia scarcely comes into the resorcinol.

Preferably, the thermally cracked product distilled out from the thermal cracking zone is taken out in the liquid state by cooling it to a temperature above the melting point of the thermal cracking product, for example to 80° to 130° C. If the resulting product is shaken with the same volume of water as in the method of the above-cited Japanese Patent Publication No. 16722/61, the yield of resorcinol is sufficiently high even though the pH of water measured after shaking is less than 4. This result is unexpected from the technique disclosed in the above-cited Japanese Patent Publication No. 16722/61.

In the method of this invention, resorcinol can be obtained as crystals by a simple procedure of dissolving the cracking product containing resorcinol distilled out by the thermal cracking in an aromatic hydrocarbon at a temperature of about 70° to about 110° C., and then cooling the solution. High-purity resorcinol can be obtained by isolating the resorcinol crystals by a solid-liquid separating means such as filtration or centrifugal separation, optionally recrystallizing or washing them, and then drying the crystals.

According to the method of this invention, the recovery yield of resorcinol in the thermal cracking is high, and the recovery of resorcinol from the thermally cracked product can be easily performed in a high yield.

The following examples illustrate the invention in greater details.

EXAMPLES 1 TO 7 AND COMPARATIVE EXAMPLES 1 TO 6

The m-DIPB oxidation product was subjected to acid cleavage in a mixture of acetone and toluene. The toluene and acetone were distilled off from the reaction mixture to afford 4818 g of an anhydrous product having the following composition.

| | |
|---|---|
| Low-boiling by-products | 23.6% by weight |
| Resorcinol | 33.1% by weight |
| High-boiling by-products | 43.3% by weight |

A 300 ml three-necked flask was charged with 200 g of the above-mentioned product (containing 66.2 g of resorcinol) and each of the catalysts shown in Table 1, and mounted on a distillation device having five sieve trays. The bottom of the distillation column was heated to 250° C. by a mantle heater, and the above product was thermally cracked for 3 hours while distilling the resorcinol fraction under reduced pressure. To the distillate was added 1.5 times its amount of toluene, and the mixture was heated to 90° C. to form a homogeneous phase. It was cooled to 30° C. to crystallize resorcinol. By centrifugal separation, crude resorcinol crystals were obtained. The crude crystals were washed with an equal amount of toluene, and dried to obtain resorcinol. The results are shown in Table 1.

TABLE 1

| | Catalyst | | Temperature (°C.) | Pressure (mmHg . G) | Amount of resorcinol recovered (g) | Ratio of resorcinol recovered (%) (*1) | Purity (%) of resorcinol after purification (*2) |
|---|---|---|---|---|---|---|---|
| | Compound | Amount (% by weight) | | | | | |
| Example | | | | | | | |
| 1 | (NH$_4$)$_2$SO$_4$ | 0.10 | 250 | 8 | 76.8 | 116 | 99.5 |
| 2 | " | 0.15 | " | " | 77.9 | 118 | 99.6 |
| 3 | " | 0.20 | " | " | 76.1 | 115 | 99.5 |
| 4 | NH$_4$HSO$_4$ | 0.10 | " | " | 76.4 | 115 | 99.6 |
| 5 | " | 0.15 | " | " | 80.1 | 121 | 99.6 |
| 6 | " | 0.20 | " | " | 77.2 | 117 | 99.5 |
| 7 | " | 0.20 | " | 20 | 76.1 | 115 | 99.6 |
| Comparative Example | | | | | | | |
| 1 | None | | " | 8 | 72.3 | 109 | 99.6 |
| 2 | " | | " | 20 | 71.2 | 108 | 99.3 |
| 3 | NH$_4$NO$_3$ | 0.15 | " | 8 | 68.9 | 104 | 99.5 |
| 4 (*3) | (NH$_4$)$_2$SO$_4$ | 0.15 | " | 80 | 73.6 | 111 | 98.7 |
| 5 (*4) | None | | " | 760 | 66.2 | 100 | 99.2 |
| 6 (*5) | " | | " | 80 | 73.6 | 111 | 98.5 |

(*1) Based on the amount of resorcinol fed.
(*2) Measured in accordance with JIS K9032-1961.
(*3) Thermal cracking was performed while blowing steam at a rate of 33 g/hr. To the distilled aqueous phase was added 1.5 times its amount of toluene to extract impurities from the aqueous phase. Water was distilled off from the aqueous phase, and resorcinol was recovered by fractional distillation.
(*4) Thermal cracking was performed while blowing nitrogen gas under atmospheric pressure at a rate of 40 ml/hr.
(*5) Thermal cracking was performed while blowing steam at a rate of 33 g/hr.

What we claim is:

1. A method for recovering resorcinol from the high-boiling by-products formed by the acid-cleavage of m-diisopropylbenzene dihydroperoxide which comprises thermally cracking the high-boiling by-products under substantially anhydrous conditions and without supplying any inert gas, said thermal cracking being carried out in the presence of at least one ammonium compound selected from the group consisting of ammonium sulfate and ammonium bisulfate at a temperature of about 170° C. to about 350° C. and at a pressure of less than 50 mm Hg gauge and recovering resorcinol therefrom.

2. The method of claim 1 wherein said thermal cracking is carried out at a pressure of not more than 40 mm Hg gauge.

3. The method of claim 1 which further comprises distilling the thermally cracked product to recover resorcinol therefrom, dissolving the recovered resorcinol in an aromatic hydrocarbon solvent at a temperature of about 70° C. to about 110° C. and cooling the solution to obtain crystalline resorcinol.

4. The method of claim 1 wherein the thermal cracking is carried out at a pressure of from about 5 to about 30 mm Hg gauge.

5. The method of claim 1 wherein the amount of the ammonium compound is about 0.01 to about 5% by weight, based on the weight of the raw materials to be thermally cracked.

6. The method of claim 1 wherein the thermal cracking is carried out at a temperature of about 200° C. to about 300° C.

7. The method of claim 6 wherein the thermal cracking is carried out at a pressure of from about 5 to about 30 mm Hg gauge.

8. The method of claim 7 wherein the amount of the ammonium compound is about 0.05 to about 0.25% by weight, based on the weight of the raw materials to be thermally cracked.

9. The method of claim 8 which further comprises distilling the thermally cracked product to recover resorcinol therefrom, dissolving the resorcinol in an aromatic hydrocarbon solvent at a temperature of about 70° C. to about 110° C. and cooling the solution to obtain crystalline resorcinol.

* * * * *